US012042284B2

(12) United States Patent
Yao et al.

(10) Patent No.: US 12,042,284 B2
(45) Date of Patent: Jul. 23, 2024

(54) IMPLANTABLE POLYMER SURFACES EXHIBITING REDUCED IN VIVO INFLAMMATORY RESPONSES

(71) Applicant: MEDTRONIC MINIMED, INC., Northridge, CA (US)

(72) Inventors: Jia Yao, Tarzana, CA (US); Daniel E. Pesantez, Canoga Park, CA (US); Anuradha Biswas Bhatia, McLean, VA (US); Akhil Srinivasan, Sherman Oaks, CA (US); Guangping Zhang, Calabasas, CA (US); Andrea Varsavsky, Santa Monica, CA (US); Raghavendhar Gautham, Los Angeles, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 1700 days.

(21) Appl. No.: 15/878,313

(22) Filed: Jan. 23, 2018

(65) Prior Publication Data

US 2019/0223771 A1 Jul. 25, 2019

(51) Int. Cl.
*A61B 5/1486* (2006.01)
*A61B 5/145* (2006.01)
(Continued)

(52) U.S. Cl.
CPC ........ *A61B 5/14865* (2013.01); *A61B 5/1451* (2013.01); *A61B 5/14532* (2013.01);
(Continued)

(58) Field of Classification Search
CPC ............ A61B 5/14532; A61B 5/14865; A61B 5/0002; A61M 2230/201
See application file for complete search history.

(56) References Cited

U.S. PATENT DOCUMENTS

| 4,755,173 A | 7/1988 | Konopka et al. |
| 5,391,250 A | 2/1995 | Cheney, II et al. |

(Continued)

FOREIGN PATENT DOCUMENTS

| CN | 102725629 A | 10/2012 |
| CN | 105073001 A | 11/2015 |
| EP | 2344024 | 7/2011 |

OTHER PUBLICATIONS

Paul et al., Topographical control of human macrophages by a regularly microstructured polyvinylidene fluoride surface, Biomaterials, vol. 29, Issue 30, 2008, pp. 4056-4064, ISSN 0142-9612 (Year: 2008).*

(Continued)

*Primary Examiner* — Tse W Chen
*Assistant Examiner* — Michael A Catina
(74) *Attorney, Agent, or Firm* — Gates & Cooper LLP

(57) ABSTRACT

Embodiments of the invention provide optimized polymeric surfaces adapted for use with implantable medical devices as well as methods for making and using such polymeric surfaces. These polymer surfaces have a constellation of features that function to inhibit or avoid an inflammatory immune response generated by implantable medical devices. Typical embodiments of the invention include an implantable glucose sensor used in the management of diabetes having a polymer surface with the disclosed constellation of features.

4 Claims, 11 Drawing Sheets

(51) Int. Cl.
*A61L 31/04* (2006.01)
*A61L 31/14* (2006.01)
*C09D 5/16* (2006.01)
*C12Q 1/00* (2006.01)
*C12Q 1/26* (2006.01)
*C12Q 1/54* (2006.01)
*A61B 5/00* (2006.01)

(52) U.S. Cl.
CPC ............... *A61L 31/04* (2013.01); *A61L 31/14* (2013.01); *C09D 5/1681* (2013.01); *C12Q 1/006* (2013.01); *C12Q 1/26* (2013.01); *C12Q 1/54* (2013.01); *A61B 5/41* (2013.01); *A61L 2400/18* (2013.01)

(56) References Cited

U.S. PATENT DOCUMENTS

| | | |
|---|---|---|
| 5,485,408 A | 1/1996 | Blomquist |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 2005/0004438 A1* | 1/2005 | Ward .................. A61B 5/14542 29/592 |
| 2007/0123819 A1 | 5/2007 | Mernoe et al. |
| 2010/0160861 A1 | 6/2010 | Causey, III et al. |
| 2014/0163346 A1* | 6/2014 | Pesantez ............ A61B 5/14532 600/347 |
| 2015/0314015 A1 | 11/2015 | Leamon et al. |
| 2017/0157380 A1* | 6/2017 | Ross ...................... A61P 29/00 |

OTHER PUBLICATIONS

PCT International Search Report & Written Opinion dated Apr. 2, 2019 for PCT Application No. PCT/US2019/014568.

Bacakova, L., et al., "Modulation of cell adhesion, proliferation and differentiation on materials designed for body implants", Biotechnology Advances, 2011, pp. 739-767, vol. 29.

Chinese Office Action dated Jan. 21, 2024 for Chinese Application No. 201980006819.

* cited by examiner

IMPLANTABLE POLYMER SURFACES EXHIBITING REDUCED IN VIVO INFLAMMATORY RESPONSES

TECHNICAL FIELD

The present invention relates to methods and materials useful for implantable medical devices, such as glucose sensors used in the management of diabetes.

BACKGROUND OF THE INVENTION

Patient responses to implanted foreign materials present challenges in the design of medical devices. These patient responses are typically characterized by the infiltration of inflammatory cells such as macrophages and their chronic activation, which can lead to the formation of a fibrous capsule at the site of implantation. This capsule typically functions to isolate the foreign body from the host immune system, and can be detrimental to the function of many medical devices including for example implanted biosensors as well as cardiovascular and orthopedic implants etc. The dense, collagen-rich tissue of a capsule may prevent diffusion of small molecules such as glucose to and from the implanted device. While efforts to reduce the immune response to implanted biomaterials have been somewhat successful, the conventional approaches have not been sufficient in addressing the effects of foreign body responses on implanted device function.

The quantitative determination of analytes in humans and mammals is of great importance in the diagnosis and maintenance of a number of pathological conditions. For this reason, implantable analyte sensors are used to monitor a wide variety of compounds including in vivo analytes. The determination of glucose concentrations in body fluids is of particular importance to diabetic individuals, individuals who must frequently check glucose levels in their body fluids to regulate the glucose intake in their diets. The results of such tests can be crucial in determining what, if any, insulin and/or other medication need to be administered. Unfortunately, the mammalian host response to implanted glucose sensors can inhibit the diffusion of glucose to and from the implanted glucose sensor, a phenomena which can compromise the accuracy of sensor readings over time.

Thus, there is a need in the art for implantable devices such as glucose sensors that can avoid or minimize host immune responses. Embodiments of the invention disclosed herein meet this as well as other needs.

SUMMARY OF THE INVENTION

The invention disclosed herein provides medical devices having polymer surfaces designed to contact an in vivo environment in order to provide the devices with enhanced functional and/or material properties, for example an ability to avoid or inhibit tissue inflammatory responses when implanted in vivo. The instant disclosure further provides methods for making and using such sensors. As discussed in detail below, typical embodiments of the invention relate to the use of a sensor device that measures a concentration of an aqueous analyte of interest or a substance indicative of the concentration or presence of the analyte in vivo. In illustrative embodiments, the sensor is used for continuous glucose monitoring in diabetic patients.

The invention disclosed herein has a number of embodiments. One embodiment is a medical device comprising a surface formed from a polymer and adapted to contact an in vivo environment. Typically, this surface comprises a polymer composition having a constellation of characteristics including a carbon-to-oxygen ratio of >5, and a surface hydrophobicity of between 75° and 90°. In addition, the surface further exhibits a topography characterized by at least one of: grooves having an average peak-to-valley height of between 0.3 μm and 5 μm; or wells having an average peak-t0alley height of between 1 μm and 2 μm; or grids having an average peak-to-valley height of between 2 μm and 4 μm. This selected constellation of surface elements functions so that, when exposed to the surface comprising the polymer composition, RAW264.7 macrophages are influenced in a manner that inhibits their differentiation into an inflammatory (M1) phenotype, and/or influenced in a manner that facilitates their differentiation into an anti-inflammatory (M2) phenotype.

In some embodiments of the invention, when exposed to the surface comprising the polymer compositions of the invention disclosed herein, RAW264.7 macrophages exhibit a decrease in MIP-1α polypeptide expression of at least 10% and/or a decrease in adherence to the surface as compared to an equivalent polymer surfaces not having a surface topography characterized by grooves having an average peak-to-valley height of between 0.3 μm and 5 μm; and/or equivalent polymer surfaces not having a surface topography characterized by wells having an average peak-to-valley height of between 1 μm and 2 μm; and/or equivalent polymer surfaces not having a surface topography characterized by grids having an average peak-to-valley height of between 2 μm and 4 μm; equivalent polymer surfaces not having a surface characterized by: a carbon-to-oxygen ratio of >5; and/or equivalent polymer surfaces not having a surface hydrophobicity of between 75° and 90°.

A related embodiment of the invention is a method of avoiding and inflammatory response to an implanted medical device comprising implanting the device having a surface adapted to contact an in vivo environment, the surface comprising a polymer composition having a constellation of characteristics including a carbon-to-oxygen ratio of >5, and a surface hydrophobicity of between 75° and 90°. The polymer surfaces of the invention further exhibit a topography characterized by at least one of: grooves having an average peak-to-valley height of between 0.3 μm and 5 μm; or wells having an average peak-to-valley height of between 1 μm and 2 μm; or grids having an average peak-to-valley height of between 2 μm and 4 μm In such embodiments, the surface avoids an inflammatory response by having surface characteristics such that when exposed to the surface comprising the polymer composition, RAW264.7 macrophages are influenced to differentiate into an anti-inflammatory (M2) phenotype (and/or avoid differentiation into the inflammatory (M1) phenotype). Typically, when exposed to the surface comprising the polymer composition, RAW264.7 macrophages exhibit a decrease in MIP-1α polypeptide expression of at 10% and also exhibit a decrease in adherence to the surface of at least 10% as compared to an equivalent polymer surface not having the surface characteristics of the polymers disclosed herein, Yet another embodiment of the invention is a method of using a laser to modify the surface of a polymer composition to form a laser ablated polymer composition having a constellation of defined characteristics including, a carbon-to-oxygen ratio of >5, and a surface hydrophobicity of between 75° and 90°. In addition, with this laser ablation methodology, the surface further exhibits a topography characterized by at least one of: grooves having an average peak-to-valley height of between 0.3 μm and 5 μm; or wells having an average peak-to-valley height of between 1 μm and 2 μm; or grids having an average peak-to-valley height of between 2 μm and 4 μm. As noted above, this constellation of surface properties at the polymer surface reduces an macrophage inflammatory response by having characteristics such that when exposed to the surface comprising the polymer composition, RAW264.7 macrophages are influenced in a manner that inhibits their differentiation into an inflammatory (M1) phenotype, and/or influenced in a manner that facilitates their differentiation into an anti-inflammatory (M2) phenotype.

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

DETAILED DESCRIPTION OF THE INVENTION

Figure 1A:
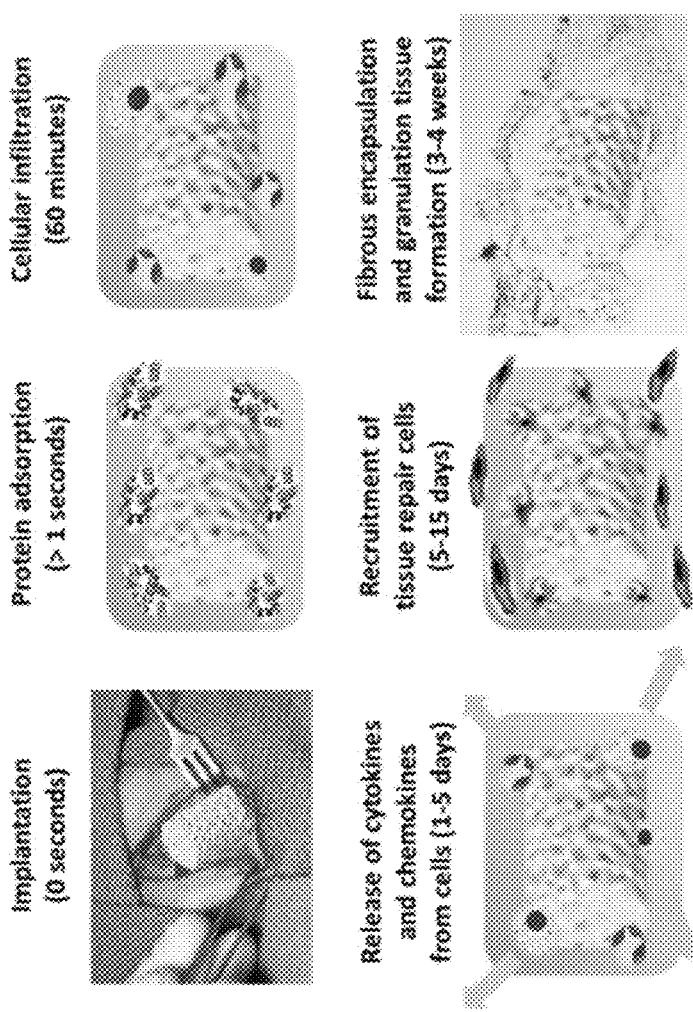
FIG. 1A shows a general timeline of tissue response against implanted biomaterials (Prior Art).
Figure 1B:
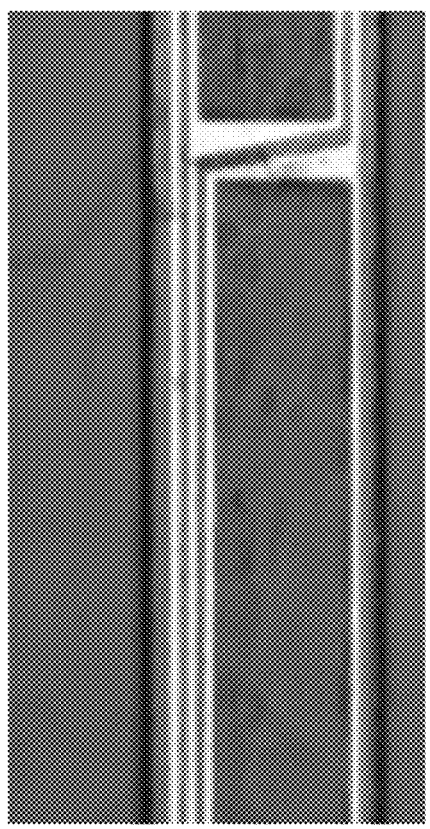
FIG. 1B is a photograph showing RAW264.7 macrophage cells cultured on glucose sensor surface demonstrated minimal cell adhesion on a GLM surface.
Figure 1C:
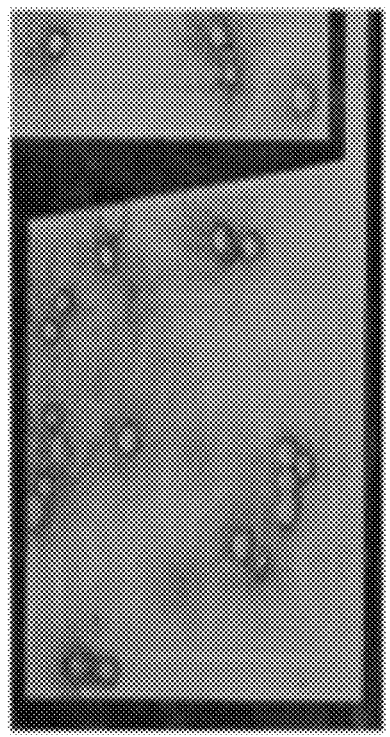
FIG. 1C is a photograph showing RAW264.7 macrophage cells cultured on glucose sensor surface demonstrated excessive macrophage cell adhesion on a polyimide surface.
Figure 1D:
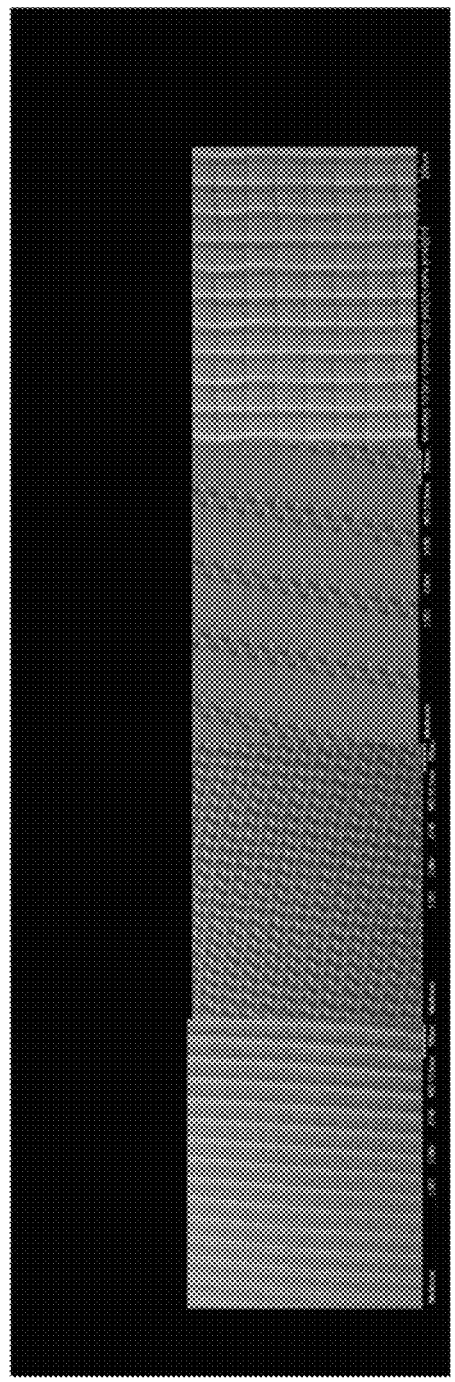
FIG. 1D shows four examples of surface topography embodiments created by different laser ablation settings. From left to right, the first panel/example shows grooves (formed with Laser wavelength of 193 nm, 900 mJ/cm2, 0.5 mm/s, 200 Hz), the second panel shows dense wells (formed with Laser wavelength of 355 nm, 8 mW, 10 mm/s, 100 Hz), the third panel shows scattered wells (formed with Laser wavelength of 355 nm, 8 mW, 10 mm/s, 100 Hz), and the last panel shows grids (formed with Laser wavelength of 355 nm, 8 mW, 10 mm/s, 100 Hz).
Figure 1E:
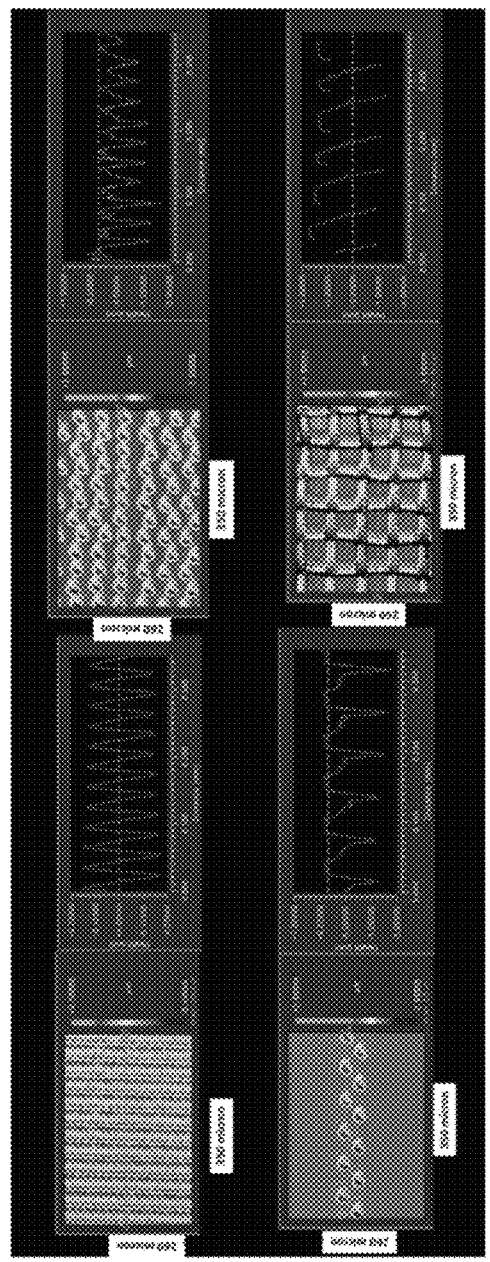
FIG. 1E shows interferometry data on surface morphology of different embodiments including data from grooves (upper left panel), dense wells (upper right panel), scattered wells (lower left panel) and grid (lower right panel).

Unless otherwise defined, all terms of art, notations, and other scientific terms or terminology used herein are intended to have the meanings commonly understood by those of skill in the art to which this invention pertains. In some cases, terms with commonly understood meanings may be defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted. A number of terms are defined below.

All numbers recited in the specification and associated claims that refer to values that can be numerically characterized with a value other than a whole number (e.g. the diameter of a circular disc) are understood to be modified by the term "about". Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Furthermore, all publications mentioned herein are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further the actual publication dates may be different from those shown and require independent verification.

The term "analyte" as used herein is a broad term and is used in its ordinary sense, including, without limitation, to refer to a substance or chemical constituent in a fluid such as a biological fluid (for example, blood, interstitial fluid, cerebral spinal fluid, lymph fluid or urine) that can be analyzed. Analytes can include naturally occurring substances, artificial substances, metabolites, and/or reaction products. In common embodiments, the analyte is glucose. However, embodiments of the invention can be used with sensors designed for detecting a wide variety other analytes. Illustrative analytes include but are not limited to, lactate as well as salts, sugars, proteins fats, vitamins and hormones that naturally occur in vivo (e.g. in blood or interstitial fluids). The analyte can be naturally present in the biological fluid or endogenous; for example, a metabolic product, a hormone, an antigen, an antibody, and the like. Alternatively, the analyte can be introduced into the body or exogenous, for example, a contrast agent for imaging, a radioisotope, a chemical agent, a fluorocarbon-based synthetic blood, or a drug or pharmaceutical composition, including but not limited to insulin. The metabolic products of drugs and pharmaceutical compositions are also contemplated analytes.

The term "sensor" for example in "analyte sensor," is used in its ordinary sense, including, without limitation, means used to detect a compound such as an analyte. A "sensor system" includes, for example, elements, structures and architectures (e.g. specific 3-dimensional constellations of elements) designed to facilitate sensor use and function. Sensor systems can include, for example, compositions such as those having selected material properties, as well as electronic components such as elements and devices used in signal detection and analysis (e.g. current detectors, monitors, processors and the like).

As discussed in detail below, embodiments of the invention relate to laser ablated polymer surfaces having surface characteristics that are useful with implantable medical devices. While the polymers of the invention can be adapted for use with a wide variety of such devices, the illustrative embodiments focused on in this disclosure are analyte sensors, typically electrochemical sensors that measure a concentration of an analyte of interest or a substance indicative of the concentration or presence of the analyte in fluid (e.g. glucose). However, the laser ablated polymer surfaces disclosed herein can be used in a wide variety of other medical devices, including devices implanted long term (e.g. devices implanted more than one month) such as orthopedics device, dental implants, stents, pacemakers, catheters and the like as well as devices implanted short term (e.g. devices implanted less than one month) such as catheters, CGM sensors, tubing for infusion sets and the like.

Embodiments of the invention disclosed herein provide sensors of the type used, for example, in subcutaneous or transcutaneous monitoring of blood glucose levels in a diabetic patient. A variety of implantable, electrochemical biosensors have been developed for the treatment of diabetes and other life-threatening diseases. Many existing sensor designs use some form of immobilized enzyme to achieve their bio-specificity. Embodiments of the invention described herein can be adapted and implemented with a wide variety of known electrochemical sensors, including for example, U.S. Patent Application No. 20050115832, U.S. Pat. Nos. 6,001,067, 6,702,857, 6,212,416, 6,119,028, 6,400,974, 6,595,919, 6,141,573, 6,122,536, 6,512,939 5,605,152, 4,431,004, 4,703,756, 6,514,718, 5,985,129, 5,390,691, 5,391, 250, 5,482,473, 5,299,571, 5,568,806, 5,494,562, 6,120,676, 6,542,765, 7,033,336 as well as PCT International Publication Numbers WO 01/58348, WO 04/021877, WO 03/034902, WO 03/035117, WO 03/035891, WO 03/023388, WO 03/022128, WO 03/022352, WO 03/023708, WO 03/036255, WO03/036310 WO 08/042,625, and WO 03/074107, and European Patent Application EP 1153571, the contents of each of which are incorporated herein by reference.

Illustrative Embodiments of the Invention and Associated Characteristics

Embodiments of the invention disclosed herein provide medical devices designed to include polymer surfaces that provide the devices with enhanced functional and/or material properties, for example an ability to avoid or inhibit tissue inflammatory responses when implanted in vivo. The disclosure further provides methods for making and using such devices. In some embodiments, the implantable device is a subcutaneous, intramuscular, intraperitoneal, intravascular or transdermal device. As discussed in detail below, some embodiments of the invention relate to the use of a sensor device that is implanted to measure a concentration of an aqueous analyte of interest or a substance indicative of the concentration or presence of the analyte in vivo. Typically, the sensor can be used for continuous glucose monitoring.

The invention disclosed herein has a number of embodiments. One embodiment is a medical device comprising a surface formed from a laser ablated polymer surface that has been adapted/modified to contact in vivo environments comprising macrophages. Typically, this laser ablated polymer surface comprises a polymer composition having a constellation of characteristics including a carbon-to-oxygen ratio of >5, and a surface hydrophobicity of between 75° and 90°. In addition, the surface further exhibits a topography characterized by at least one of: grooves having an average peak-to-valley height of between 0.3 µm and 5 µm; or wells having an average peak-to-valley height of between 1 µm and 2 µm; or grids having an average peak-to-valley height of between 2 µm and 4 µm. In illustrative embodiments of the invention, the polymer comprises a polyimide, a polyamide, a polyethylene terephthalate, a ethylene tetrafluoroethylene, a polyether block amide, a polycarbonate, a polypropylene, a polyethylene, a polystyrene, a polyvinyl chloride, a polymethyl methacrylate, an acrylonitrile butadiene, a polyetheretherketone, a polyurethane or an epoxy.

As is known in the art, classically activated macrophages (M1) are proinflammatory effectors, while alternatively activated macrophages (M2) exhibit anti-inflammatory properties. The selected constellation of surface elements of the laser ablated polymers functions so that, when exposed to the surface comprising the polymer composition, RAW264.7 macrophages are influenced to differentiate into an anti-inflammatory (M2) phenotype and/or inhibited from differentiating into an inflammatory (M1) phenotype (e.g. as shown by decreases in MIP-1α expression, or by undergoing fewer morphological changes and elongations as compared RAW264.7 macrophage cells contacting a control surface not having the constellation of elements disclosed herein). This is significant because macrophages, especially their activation state, are closely related to the progression of the inflammatory response that can be detrimental to the function of implanted devices. (see, e.g. Anderson Annu. Rev. Mater. Res. 2001. 31:81-110; Li et al., Hum Exp Toxicol. 2017 Jan. 1: 960327117714039. doi: 10.1177/ 0960327117714039. [Epub ahead of print]; Kianoush et al., J Biomed Mater Res A. 2017 September; 105(9):2499-2509. doi: 10.1002/jbm.a.36107. Epub 2017 Jun. 6; and Chen et al., Diabetes Metab Res Rev. 2015 November; 31(8):781-9. doi: 10.1002/dmrr.2761. Epub 2015 Nov. 20).

Figure 1F:
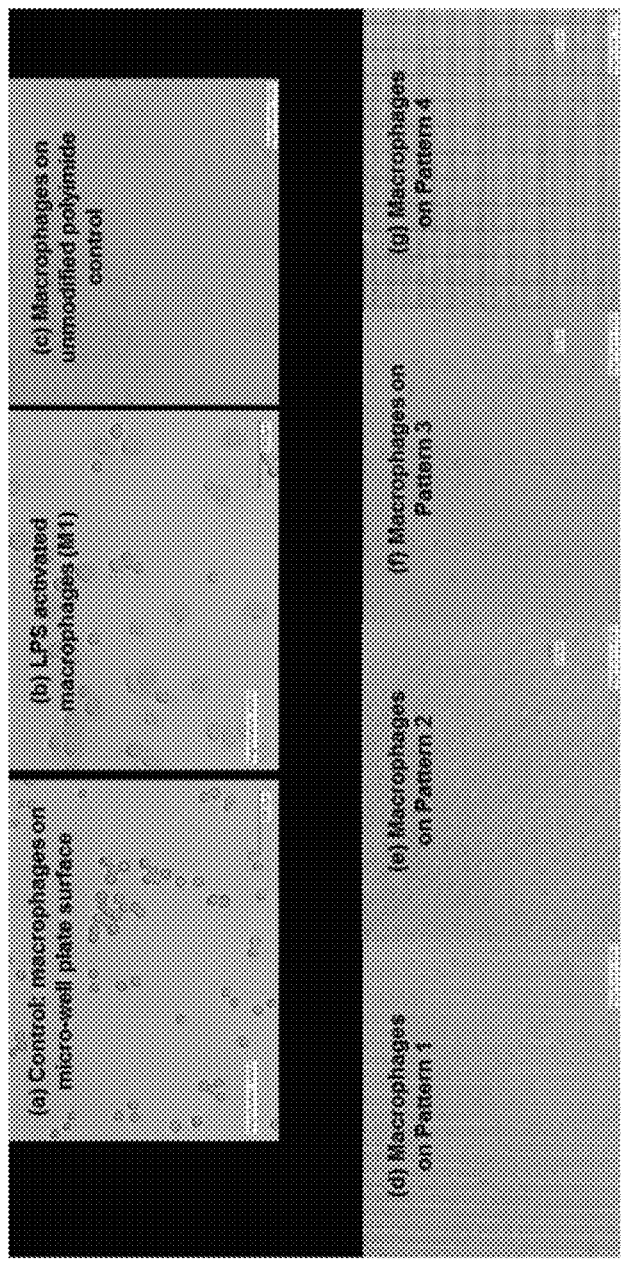
FIG. 1F shows examples of macrophage adhesion and morphology from different embodiments of the invention: (a) control: macrophages adhere onto the surface of micro-well plate in native round morphology; (b) positively activated macrophages (M1) adhere onto micro-well plate with signature elongated morphology; (c) macrophages adhere onto unmodified polyimide surface in native round morphology; (d) (e) (f) (g) macrophages adhesion and morphology on modified surfaces from grooves, dense wells, scattered wells and grid. Less morphological changes and elongations in RAW264.7 macrophage cells are observed on these four groups compared to control RAW264.7 macrophage cells from (c).
Figure 1G:
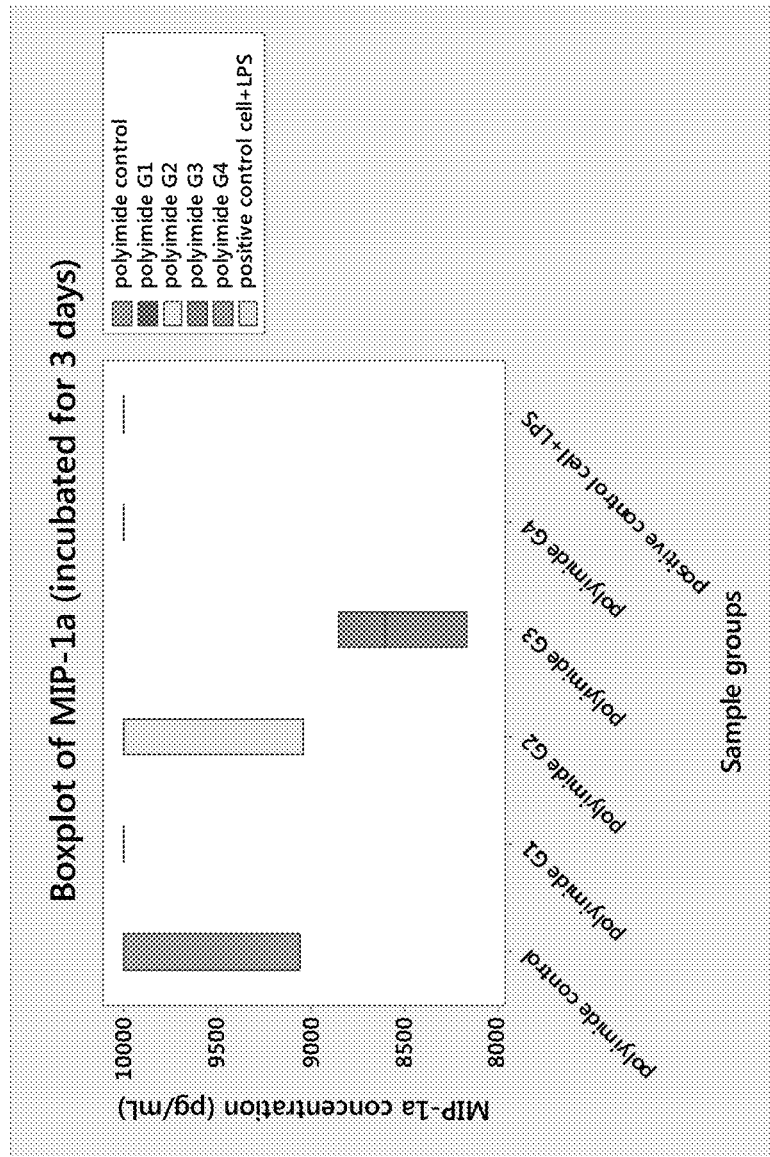
FIG. 1G provides data showing that laser beam patterned surfaces demonstrate lower RAW264.7 macrophage inflammatory response based on cytokine quantification. Graphic data from cytokine studies with scattered well morphology embodiment demonstrated lower level of MIP-1α (pro-inflammatory cytokine) as compared to unmodified polyimide control sample.
Figure 1H:
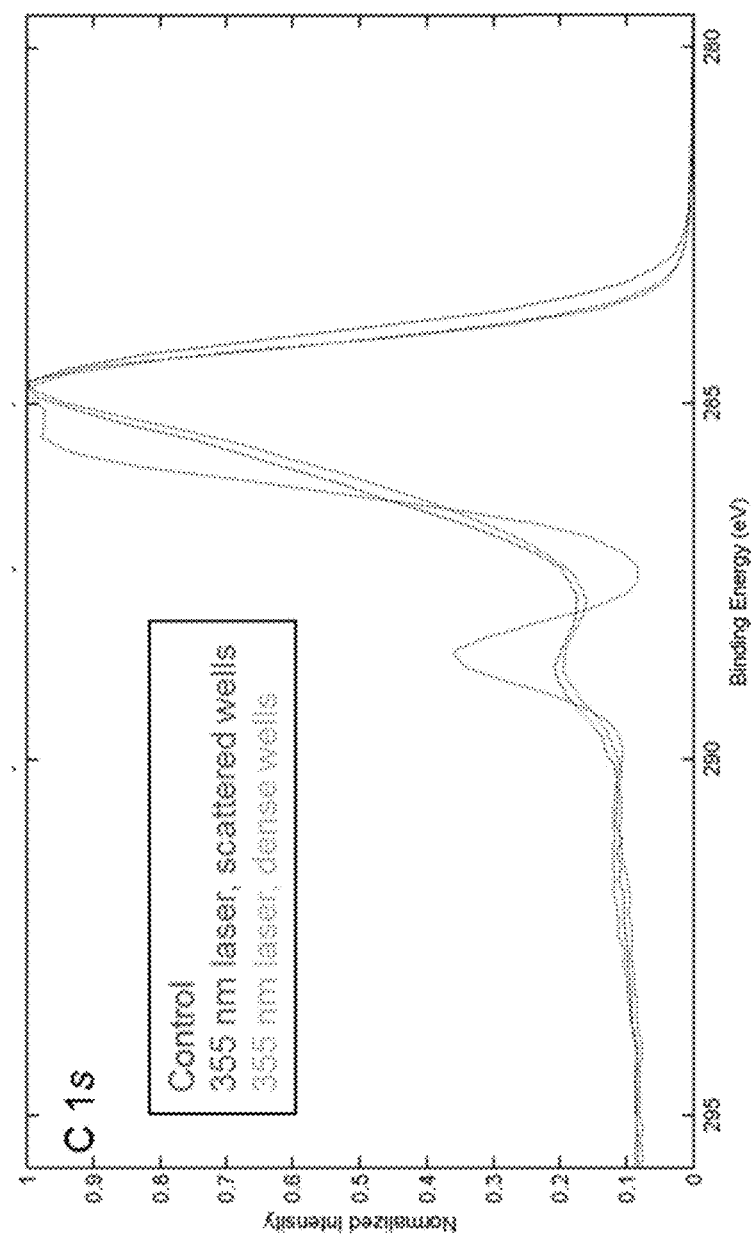
FIG. 1H shows data on surface chemical properties as determined by X-ray Photoelectron Spectroscopy (XPS) analysis. This XPS analysis demonstrated change in carbon chemistry of polyimide before and after laser ablation based on high resolution C 1 s spectral envelope. Laser ablated regions show a shift towards amorphous carbon (C—C) centered at approximately 284.8 eV.
Figure 1I:
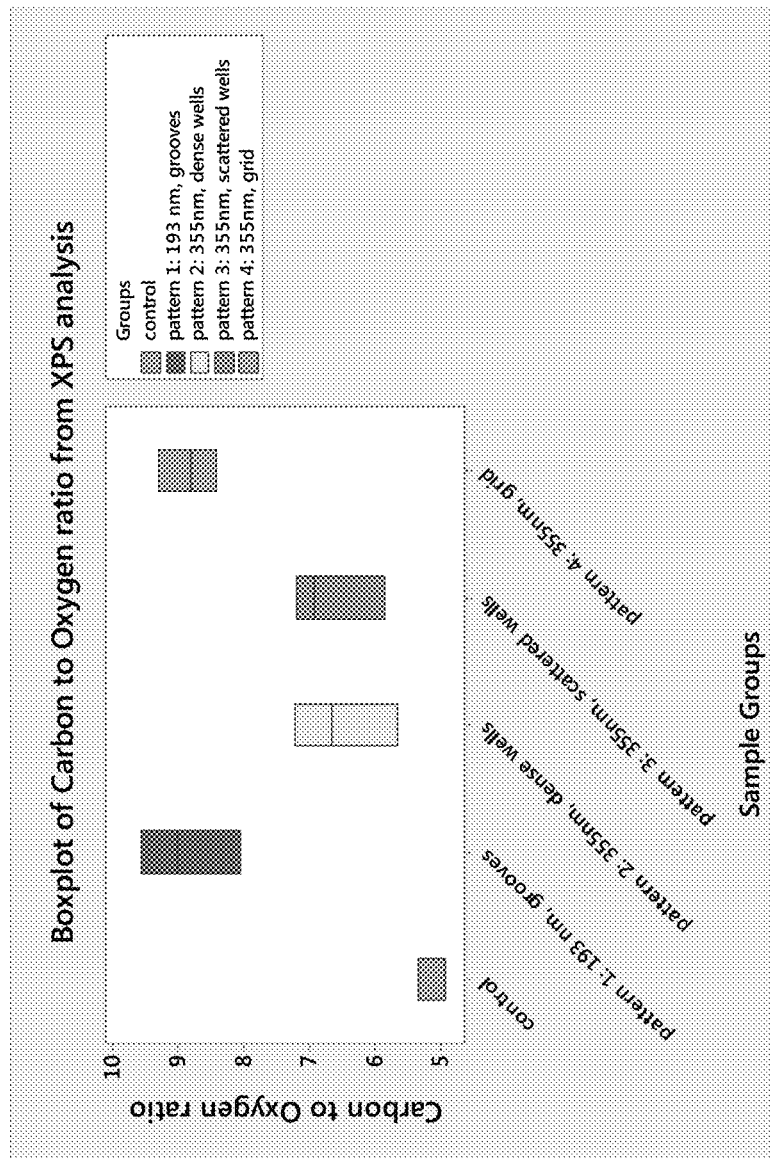
FIG. 1I provides data showing that XPS analysis demonstrated that laser ablation altered surface chemical property. Laser ablated samples demonstrated higher carbon-to-oxygen ration compared to control samples.

Certain embodiments of the invention comprise medical devices having a polymer surface of the invention that show quantitative effects on macrophages. For example, in some embodiments of the invention, when exposed to the surface comprising the polymer compositions of the invention disclosed herein, RAW264.7 macrophages exhibit a decrease in MIP-1α polypeptide expression of at least 10% as compared to an equivalent polymer surfaces not having a surface topography characterized by grooves having an average peak-to-valley height of between 0.3 μm and 5 μm; and/or equivalent polymer surfaces not having a surface topography characterized by wells having an average peak-to-valley height of between 1 μm and 2 μm; and/or equivalent polymer surfaces not having a surface topography characterized by grids having an average peak-to-valley height of between 2 μm and 4 μm; equivalent polymer surfaces not having a surface characterized by: a carbon-to-oxygen ratio of >5; and/or equivalent polymer surfaces not having a surface hydrophobicity of between 75° and 90°. FIG. 1G provides data from a working embodiment of the invention having these properties.

Other embodiments of the invention comprise medical devices having a polymer surface of the invention that show other quantitative effects on macrophages. For example, in some embodiments of the invention, when exposed to the surface comprising the polymer compositions of the invention disclosed herein, RAW264.7 macrophages exhibit an adherence to the surface that is inhibited by at least 10% (and/or exhibit at least 10% less morphological changes and elongations in RAW264.7 macrophage cells) as compared to control RAW264.7 macrophage cells contacting equivalent polymer surfaces not having a surface topography characterized by grooves having an average peak-to-valley height of between 0.3 μm and 5 μm; and/or equivalent polymer surfaces not having a surface topography characterized by wells having an average peak-to-valley height of between 1 μm and 2 μm; and/or equivalent polymer surfaces not having a surface topography characterized by grids having an average peak-to-valley height of between 2 μm and 4 μm; equivalent polymer surfaces not having a surface characterized by a carbon-to-oxygen ratio of >5; and/or equivalent polymer surfaces not having a surface hydrophobicity of between 75° and 90°. FIG. 1F provides data from a working embodiment of the invention having these properties.

In typical embodiments of the invention, the implantable device comprising a polymer that contacts an in vivo tissue is a glucose sensor. In certain embodiments, the glucose sensor comprises a base layer, a working electrode, a reference electrode, and a counter electrode disposed on the base layer, an analyte sensing layer disposed over the working electrode, wherein the analyte sensing layer comprises glucose oxidase, and an analyte modulating layer disposed over the analyte sensing layer, wherein the analyte modulating layer modulates the diffusion of glucose therethrough. Optionally, the glucose sensor further comprises at least one of an interference rejection layer disposed over the working electrode, an adhesion promoting layer disposed between the analyte sensing layer and the analyte modulating layer, a protein layer disposed on the analyte sensing layer; or a cover layer disposed over the analyte modulating layer.

A related embodiment of the invention is a method of avoiding and inflammatory response to an implanted medical device comprising implanting the device having a surface adapted to contact an in vivo environment, the surface comprising a polymer composition having a constellation of characteristics including a carbon-to-oxygen ratio of >5, and a surface hydrophobicity of between 75° and 90°. In addition, the surface further exhibits a topography characterized by at least one of: grooves having an average peak-to-valley height of between 0.3 μm and 5 μm; or wells having an average peak-to-valley height of between 1 μm and 2 μm; or grids having an average peak-to-valley height of between 2 μm and 4 μm. the surface avoids an inflammatory response by having surface characteristics such that when exposed to the surface comprising the polymer composition, RAW264.7 macrophages are influenced to differentiate into an anti-inflammatory (M2) phenotype (and/or avoid differentiation into the inflammatory (M1) phenotype). This is observable by a number of phenomena disclosed herein such as the macrophages undergoing at least 10% fewer morphological changes and elongations as compared to RAW264.7 macrophage cells contacting a surface not having the constellation of characteristics disclosed herein. Optionally, the medical device is implanted in an interstitial space. In typical embodiments, the medical device is a glucose sensor. In an illustrative embodiment, the polymer is a polyimide. Typically, when exposed to the surface comprising the polymer composition, RAW264.7 macrophages exhibit a decrease in MIP-1α polypeptide expression of at 10% and also exhibit a decrease in adherence to the surface of at least 10% as compared to an equivalent polymer surface not having the surface characteristics of the polymers disclosed herein, Yet another embodiment of the invention is a method of using a laser to modify the surface of a polymer composition to form a laser ablated polymer composition having a constellation of defined characteristics including, a carbon-to-oxygen ratio of >5, and a surface hydrophobicity of between 75° and 90°. In addition, the surface further exhibits a topography characterized by at least one of: grooves having an average peak-to-valley height of between 0.3 μm and 5 μm; or wells having an average peak-to-valley height of between 1 μm and 2 μm; or grids having an average peak-to-valley height of between 2 μm and 4 μm. This constellation of surface properties at the polymers surface avoids an inflammatory response by having characteristics such that when exposed to the surface comprising the polymer composition, RAW264.7 macrophages are influenced to differentiate into an anti-inflammatory (M2) phenotype. In an illustrative embodiment, the polymer is a polyimide. The method uses art accepted methods for laser ablation and can include for example, exposing the polymer surface to a laser ablation modification process using a laser machining system coupled to a software based controller; and ablating the surface such that the surface exhibits the carbon-to-oxygen, surface hydrophobicity and surface topography characteristics disclosed herein so that the laser ablated polymer surface avoids an inflammatory response by having surface characteristics such that when exposed to the surface comprising the polymer composition, RAW264.7 macrophages are influenced to differentiate into an anti-inflammatory (M2) phenotype. In the instant invention, a system from Aerotech was used for laser processing and machining (EDU173, Software Version 2.14).

Typically, the polymer surface of the invention comprises a polyimide, a polyamide, a polyethylene terephthalate, a ethylene tetrafluoroethylene, a polyether block amide, a polycarbonate, a polypropylene, a polyethylene, a polystyrene, a polyvinyl chloride, a polymethyl methacrylate, an acrylonitrile butadiene, a polyetheretherketone, a polyurethane or an epoxy. In addition, when exposed to the surface comprising the polymer composition, RAW264.7 macrophages exhibit a decrease in MIP-1α polypeptide expression of at 10%; and/or exhibit a decrease in adherence to the surface of at least 10% as compared to an equivalent polymer surface not exposed to the laser ablation modification process and/or exhibit fewer morphological changes and elongations as compared RAW264.7 macrophage cells exposed to an equivalent polymer surface not manipulated by a laser ablation modification process. Certain embodiments of the invention further comprise disposing the laser ablated surface on an implantable medical device (e.g. a glucose sensor) in an orientation where the surface contacts macrophages when the device is implanted in vivo.

Yet another embodiment of the invention is a polymer composition that forms a surface comprising a carbon-to-oxygen ratio of >5, a surface hydrophobicity of between 75° and 90°, a surface topography characterized by grooves having an average peak-to-valley height of between 0.3 µm and 5 µm; and/or wells having an average peak-to-valley height of between 1 µm and 2 µm; and/or grids having an average peak-to-valley height of between 2 µm and 4 µm. When exposed to the surface comprising the polymer composition, RAW264.7 macrophages exhibit a decrease in MIP-1α polypeptide expression of at 10% and also exhibit a decrease in adherence to the surface of at least 10% as compared to an equivalent polymer surface not having the surface characteristics of the polymers disclosed herein (i.e. when exposed to the surface, RAW264.7 macrophages are influenced to differentiate into an anti-inflammatory (M2) phenotype).

In typical glucose sensor embodiments of the invention, electrochemical glucose sensors are operatively coupled to a sensor input capable of receiving signals from the electrochemical sensor; and a processor coupled to the sensor input, wherein the processor is capable of characterizing one or more signals received from the electrochemical sensor. In certain embodiments of the invention, the electrical conduit of the electrode is coupled to a potentiostat. Optionally, a pulsed voltage is used to obtain a signal from an electrode. In certain embodiments of the invention, the processor is capable of comparing a first signal received from a working electrode in response to a first working potential with a second signal received from a working electrode in response to a second working potential. Optionally, the electrode is coupled to a processor adapted to convert data obtained from observing fluctuations in electrical current from a first format into a second format. Such embodiments include, for example, processors designed to convert a sensor current Input Signal (e.g. ISIG measured in nA) to a blood glucose concentration.

In embodiments of the invention, the sensors comprise another biocompatible polymer region adapted to be implanted in vivo and directly contact the in vivo environment. In embodiments of the invention, the biocompatible region can comprise any polymer surface that contacts an in vivo tissue. In this way, sensors used in the systems of the invention can be used to sense a wide variety of analytes in different aqueous environments. In some embodiments, the sensor comprises a discreet probe that pierces an in vivo environment. In some embodiments of the invention, the electrode is coupled to a piercing member (e.g. a needle) adapted to be implanted in vivo. While sensor embodiments of the invention can comprise one or two piercing members, optionally such sensor apparatuses can include 3 or 4 or 5 or more piercing members that are coupled to and extend from a base element and are operatively coupled to 3 or 4 or 5 or more electrochemical sensors (e.g. microneedle arrays, embodiments of which are disclosed for example in U.S. Pat. Nos. 7,291,497 and 7,027,478, and U.S. patent Application No. 20080015494, the contents of which are incorporated by reference).

Embodiments of the invention include analyte sensor apparatuses designed to utilize the polymer surfaces disclosed herein. Such apparatuses typically include a base on which electrically conductive members are disposed and configured to form a working electrode. In some embodiments of the invention, an array of electrically conductive members is coupled to a common electrical conduit (e.g. so that the conductive members of the array are not separately wired, and are instead electrically linked as a group). Optionally, the electrical conduit is coupled to a power source adapted to sense fluctuations in electrical current of the array of the working electrode. Typically, the apparatus includes a reference electrode; and a counter electrode. Optionally one or more of these electrodes also comprises a plurality of electrically conductive members disposed on the base in an array. In some embodiments, each of the electrically conductive members of the electrode (e.g. the counter electrode) comprises an electroactive surface adapted to sense fluctuations in electrical current at the electroactive surface; and the group of electrically conductive members are coupled to a power source (e.g. a potentiostat or the like).

In some embodiments of the invention, the apparatus comprises a plurality of working electrodes, counter electrodes and reference electrodes clustered together in units consisting essentially of one working electrode, one counter electrode and one reference electrode; and the clustered units are longitudinally distributed on the base layer in a repeating pattern of units. In some sensor embodiments, the distributed electrodes are organized/disposed within a flex-circuit assembly (i.e. a circuitry assembly that utilizes flexible rather than rigid materials). Such flex-circuit assembly embodiments provide an interconnected assembly of elements (e.g. electrodes, electrical conduits, contact pads and the like) configured to facilitate wearer comfort (for example by reducing pad stiffness and wearer discomfort).

In some embodiments of the invention, an analyte sensing layer is disposed over electrically conductive members, and includes an agent that is selected for its ability to detectably alter the electrical current at the working electrode in the presence of an analyte. In the working embodiments of the invention that are disclosed herein, the agent is glucose oxidase, a protein that undergoes a chemical reaction in the presence of glucose that results in an alteration in the electrical current at the working electrode. These working embodiments further include an analyte modulating layer disposed over the analyte sensing layer, wherein the analyte modulating layer modulates the diffusion of glucose as it migrates from an in vivo environment to the analyte sensing layer. In certain embodiments of the invention, the analyte modulating layer comprises a hydrophilic comb-copolymer having a central chain and a plurality of side chains coupled to the central chain, wherein at least one side chain comprises a silicone moiety. In certain embodiments of the invention, the analyte modulating layer comprises a blended mixture of: a linear polyurethane/polyurea polymer, and a branched acrylate polymer; and the linear polyurethane/polyurea polymer and the branched acrylate polymer are blended at a ratio of between 1:1 and 1:20 (e.g. 1:2) by weight %. In working embodiments of the present invention, the signal strength and $O_2$ response of the microarray sensor electrode can be increased with the use of a 2× permselective GLM (glucose limiting membrane). Typically, this analyte modulating layer composition comprises a first polymer formed from a mixture comprising a diisocyanate; at least one hydrophilic diol or hydrophilic diamine; and a siloxane; that is blended with a second polymer formed from a mixture comprising: a 2-(dimethylamino)ethyl methacrylate; a methyl methacrylate; a polydimethyl siloxane monomethacryloxypropyl; a poly(ethylene oxide) methyl ether methacrylate; and a 2-hydroxyethyl methacrylate. Additional material layers can be included in such apparatuses. For example, in some embodiments of the invention, the apparatus comprises an adhesion promoting layer disposed between the analyte sensing layer and the analyte modulating layer.

Figure 2:
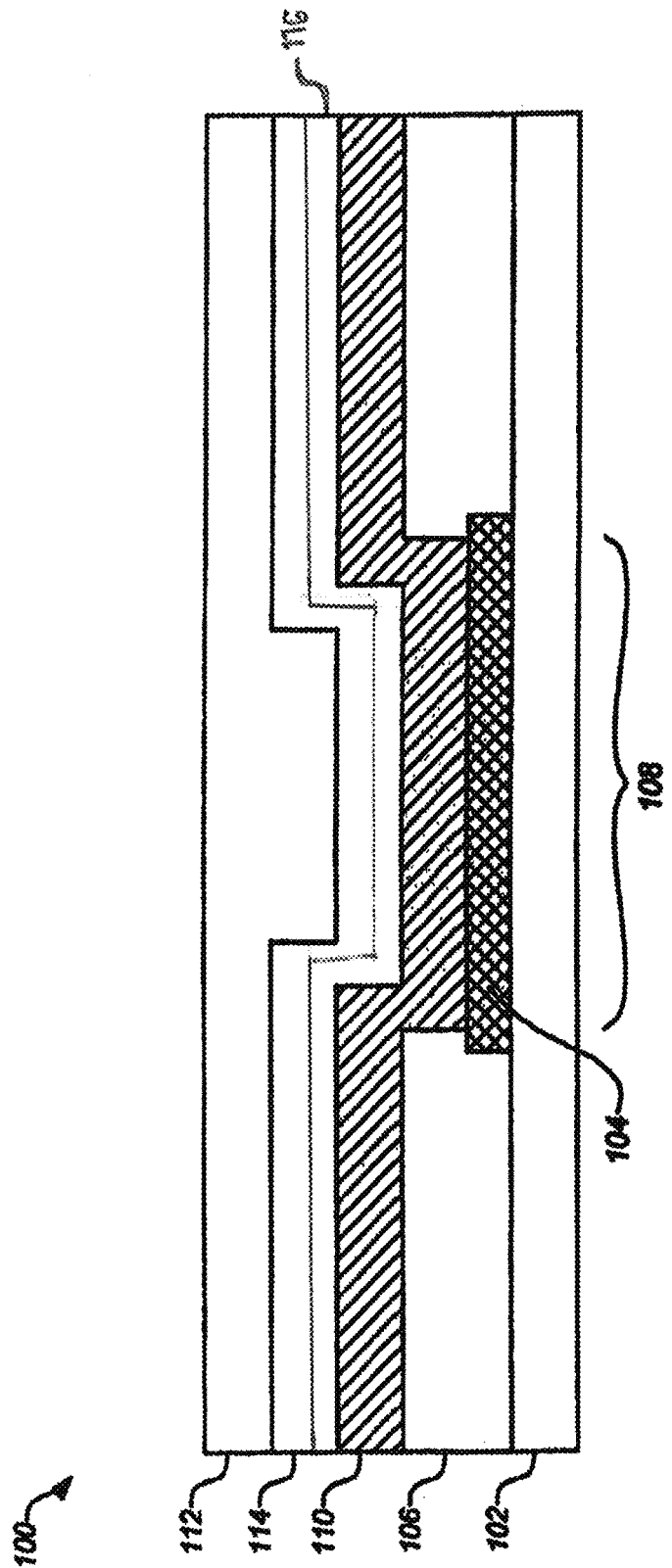
FIG. 2 shows a sensor design comprising an amperometric analyte sensor formed from a plurality of planar layered elements.

One sensor embodiment shown in FIG. 2 is a amperometric sensor 100 having a plurality of layered elements including a base layer 102 (e.g. one formed from a polymer disclosed herein), a conductive layer 104 (e.g. one comprising the plurality of electrically conductive members) which is disposed on and/or combined with the base layer 102. Typically, the conductive layer 104 comprises one or more electrodes. An analyte sensing layer 110 (typically comprising an enzyme such as glucose oxidase) can be disposed on one or more of the exposed electrodes of the conductive layer 104. A protein layer 116 can be disposed upon the analyte sensing layer 110. An analyte modulating layer 112 can be disposed above the analyte sensing layer 110 to regulate analyte (e.g. glucose) access with the analyte sensing layer 110. An adhesion promoter layer 114 is disposed between layers such as the analyte modulating layer 112 and the analyte sensing layer 110 as shown in FIG. 2 in order to facilitate their contact and/or adhesion. This embodiment also comprises a cover layer 106 such as a polymer surface coating disclosed herein can be disposed on portions of the sensor 100. Apertures 108 can be formed in one or more layers of such sensors. Amperometric glucose sensors having this type of design are disclosed, for example, in U.S. Patent Application Publication Nos. 20070227907, 20100025238, 20110319734 and 20110152654, the contents of each of which are incorporated herein by reference.

Yet another embodiment of the invention is a method of sensing an analyte within the body of a mammal. Typically, this method comprises implanting an analyte sensor comprising one or more anti-inflammatory polymer surfaces within the mammal (e.g. in the interstitial space of a diabetic individual), sensing an alteration in current at the working electrode in the presence of the analyte; and then correlating the alteration in current with the presence of the analyte, so that the analyte is sensed.

Embodiments of the invention also provide articles of manufacture and kits for observing a concentration of an analyte. In an illustrative embodiment, the kit includes a sensor comprising a polymer surface as discussed herein. In typical embodiments, the sensors are disposed in the kit within a sealed sterile dry package. Optionally the kit comprises an insertion device that facilitates insertion of the sensor. The kit and/or sensor set typically comprises a container, a label and an analyte sensor as described above. Suitable containers include, for example, an easy to open package made from a material such as a metal foil, bottles, vials, syringes, and test tubes. The containers may be formed from a variety of materials such as metals (e.g. foils) paper products, glass or plastic. The label on, or associated with, the container indicates that the sensor is used for assaying the analyte of choice. The kit and/or sensor set may include other materials desirable from a commercial and user standpoint, including buffers, diluents, filters, needles, syringes, and package inserts with instructions for use.

Specific aspects of embodiments of the invention are discussed in detail in the following sections.

Figure 3:
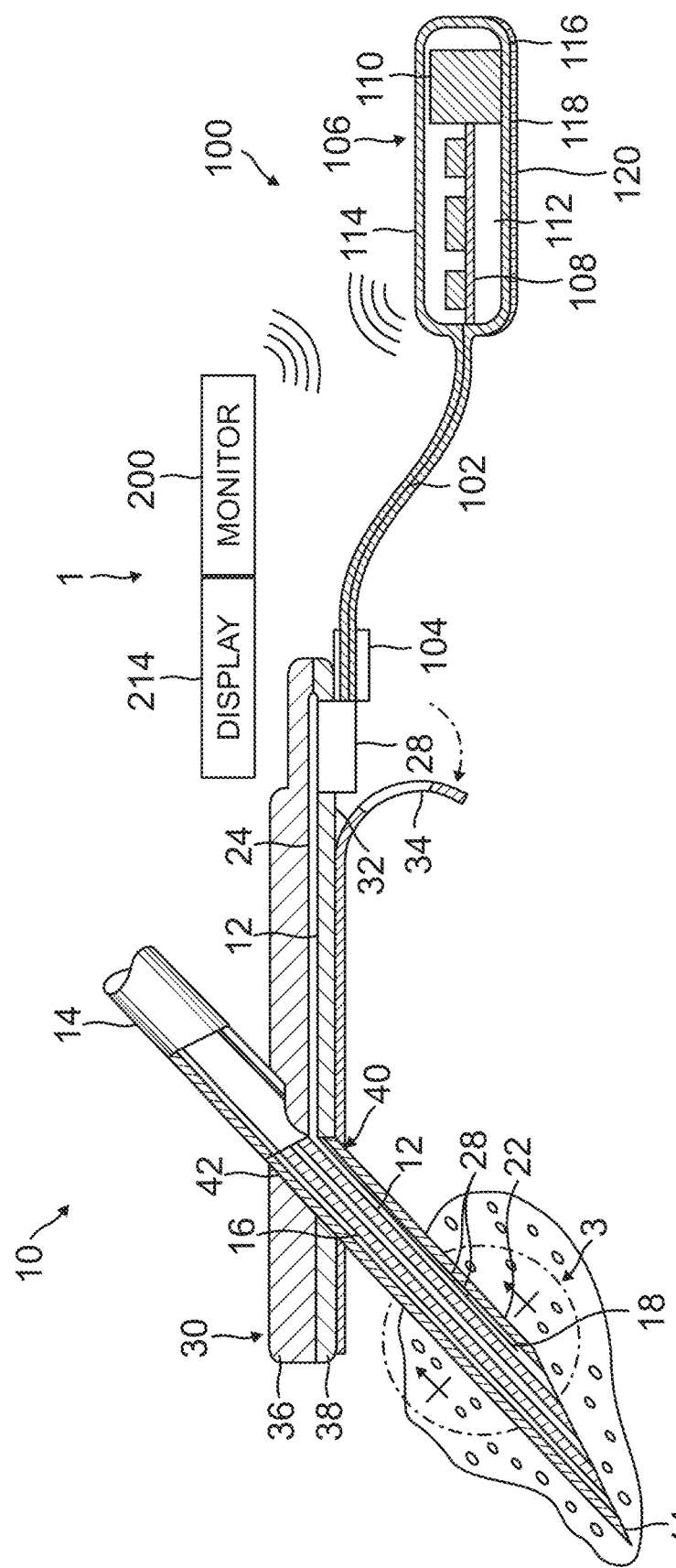
FIG. 3 provides a perspective view illustrating a subcutaneous sensor insertion set, a telemetered characteristic monitor transmitter device, and a data receiving device embodying features of the invention.

Typical Elements, Configurations and Analyte Sensor Embodiments of the Invention A. Typical Elements Found in of Embodiments of the Invention FIGS. 2 and 3 provide illustrations of various sensor and sensor system embodiments of the invention.

FIG. 2 illustrates a cross-section of a typical sensor embodiment 100 of the present invention. This sensor embodiment is formed from a plurality of components that are typically in the form of layers of various conductive and non-conductive constituents disposed on each other according to art accepted methods and/or the specific methods of the invention disclosed herein. The components of the sensor are typically characterized herein as layers because, for example, it allows for a facile characterization of the sensor structure shown in FIG. 2. Artisans will understand however, that in certain embodiments of the invention, the sensor constituents are combined such that multiple constituents form one or more heterogeneous layers. In this context, those of skill in the art understand that the ordering of the layered constituents can be altered in various embodiments of the invention.

The embodiment shown in FIG. 2 includes a base layer 102 to support the sensor 100. The base layer 102 can be made of a material such as a polymeric surface having the constellation of elements disclosed herein, a metal and/or a ceramic, which may be self-supporting or further supported by another material as is known in the art. Embodiments of the invention include a conductive layer 104 which is disposed on and/or combined with the base layer 102. Typically, the conductive layer 104 comprises one or more electrically conductive elements that function as electrodes. An operating sensor 100 typically includes a plurality of electrodes such as a working electrode, a counter electrode and a reference electrode. Other embodiments may also include a plurality of working and/or counter and/or reference electrodes and/or one or more electrodes that performs multiple functions, for example one that functions as both as a reference and a counter electrode.

As discussed in detail below, the base layer 102 and/or conductive layer 104 can be generated using many known techniques and materials. In certain embodiments of the invention, the electrical circuit of the sensor is defined by etching the disposed conductive layer 104 into a desired pattern of conductive paths. A typical electrical circuit for the sensor 100 comprises two or more adjacent conductive paths with regions at a proximal end to form contact pads and regions at a distal end to form sensor electrodes. An electrically insulating cover layer 106 such as a polymer coating can be disposed on portions of the sensor 100. Acceptable polymer coatings for use as the insulating protective cover layer 106 can include, but are not limited to polymers having the constellation of features disclosed herein, non-toxic biocompatible polymers such as silicone compounds, polyimides, biocompatible solder masks, epoxy acrylate copolymers, or the like. In the sensors of the present invention, one or more exposed regions or apertures 108 can be made through the cover layer 106 to open the conductive layer 104 to the external environment and to, for example, allow an analyte such as glucose to permeate the layers of the sensor and be sensed by the sensing elements. Apertures 108 can be formed by a number of techniques, including laser ablation, tape masking, chemical milling or etching or photolithographic development or the like. In certain embodiments of the invention, during manufacture, a secondary photoresist can also be applied to the protective layer 106 to define the regions of the protective layer to be removed to form the aperture(s) 108. The exposed electrodes and/or contact pads can also undergo secondary processing (e.g. through the apertures 108), such as additional plating processing, to prepare the surfaces and/or strengthen the conductive regions.

In the sensor configuration shown in FIG. 2, an analyte sensing layer 110 is disposed on one or more of the exposed electrodes of the conductive layer 104. Typically, the analyte sensing layer 110 is an enzyme layer. Most typically, the analyte sensing layer 110 comprises an enzyme capable of producing and/or utilizing oxygen and/or hydrogen peroxide, for example the enzyme glucose oxidase. Optionally the enzyme in the analyte sensing layer is combined with a second carrier protein such as human serum albumin, bovine serum albumin or the like. In an illustrative embodiment, an oxidoreductase enzyme such as glucose oxidase in the analyte sensing layer 110 reacts with glucose to produce hydrogen peroxide, a compound which then modulates a current at an electrode. As this modulation of current depends on the concentration of hydrogen peroxide, and the concentration of hydrogen peroxide correlates to the concentration of glucose, the concentration of glucose can be determined by monitoring this modulation in the current. In a specific embodiment of the invention, the hydrogen peroxide is oxidized at a working electrode which is an anode (also termed herein the anodic working electrode), with the resulting current being proportional to the hydrogen peroxide concentration. Such modulations in the current caused by changing hydrogen peroxide concentrations can by monitored by any one of a variety of sensor detector apparatuses such as a universal sensor amperometric biosensor detector or one of the other variety of similar devices known in the art such as glucose monitoring devices produced by Medtronic Diabetes.

In embodiments of the invention, the analyte sensing layer 110 can be applied over portions of the conductive layer or over the entire region of the conductive layer. Typically, the analyte sensing layer 110 is disposed on the working electrode which can be the anode or the cathode. Optionally, the analyte sensing layer 110 is also disposed on a counter and/or reference electrode. Methods for generating a thin analyte sensing layer 110 include brushing the layer onto a substrate (e.g. the reactive surface of a platinum black electrode), as well as spin coating processes, dip and dry processes, low shear spraying processes, ink-jet printing processes, silk screen processes and the like. In certain embodiments of the invention, brushing is used to: (1) allow for a precise localization of the layer; and (2) push the layer deep into the architecture of the reactive surface of an electrode (e.g. platinum black produced by an electrodeposition process).

Typically, the analyte sensing layer 110 is coated and or disposed next to one or more additional layers. Optionally, the one or more additional layers includes a protein layer 116 disposed upon the analyte sensing layer 110. Typically, the protein layer 116 comprises a protein such as human serum albumin, bovine serum albumin or the like. Typically, the protein layer 116 comprises human serum albumin. In some embodiments of the invention, an additional layer includes an analyte modulating layer 112 that is disposed above the analyte sensing layer 110 to regulate analyte contact with the analyte sensing layer 110. For example, the analyte modulating membrane layer 112 can comprise a glucose limiting membrane, which regulates the amount of glucose that contacts an enzyme such as glucose oxidase that is present in the analyte sensing layer. Such glucose limiting membranes can be made from a wide variety of materials known to be suitable for such purposes, e.g., silicone compounds such as polydimethyl siloxanes, polyurethanes, polyurea cellulose acetates, Nafion, polyester sulfonic acids (e.g. Kodak AQ), hydrogels or any other suitable hydrophilic membranes known to those skilled in the art.

In typical embodiments of the invention, an adhesion promoter layer 114 is disposed between the analyte modulating layer 112 and the analyte sensing layer 110 as shown in FIG. 2 in order to facilitate their contact and/or adhesion. In a specific embodiment of the invention, an adhesion promoter layer 114 is disposed between the analyte modulating layer 112 and the protein layer 116 as shown in FIG. 2 in order to facilitate their contact and/or adhesion. The adhesion promoter layer 114 can be made from any one of a wide variety of materials known in the art to facilitate the bonding between such layers. Typically, the adhesion promoter layer 114 comprises a silane compound. In alternative embodiments, protein or like molecules in the analyte sensing layer 110 can be sufficiently crosslinked or otherwise prepared to allow the analyte modulating membrane layer 112 to be disposed in direct contact with the analyte sensing layer 110 in the absence of an adhesion promoter layer 114.

B. Typical Analyte Sensor Constituents Used in Embodiments of the Invention

The following disclosure provides examples of typical elements/constituents used in sensor embodiments of the invention. While these elements can be described as discreet units (e.g. layers), those of skill in the art understand that sensors can be designed to contain elements having a combination of some or all of the material properties and/or functions of the elements/constituents discussed below (e.g. an element that serves both as a supporting base constituent and/or a conductive constituent and/or a matrix for the analyte sensing constituent and which further functions as an electrode in the sensor). Those in the art understand that these thin film analyte sensors can be adapted for use in a number of sensor systems such as those described below.

Base Constituent

Sensors of the invention typically include a base constituent (see, e.g. element 102 in FIG. 2). The term "base constituent" is used herein according to art accepted terminology and refers to the constituent in the apparatus that typically provides a supporting matrix for the plurality of constituents that are stacked on top of one another and comprise the functioning sensor. In one form, the base constituent comprises a thin film sheet of insulative (e.g. electrically insulative and/or water impermeable) material such as a polymer comprising a surface having the constellation of features disclosed herein that function to modulate immune response. This base constituent can be made of a wide variety of materials having desirable qualities such as the constellation of features disclosed herein as well as dielectric properties, water impermeability and hermeticity. Some materials include metallic, and/or ceramic and/or polymeric substrates or the like.

Conductive Constituent

The electrochemical sensors of the invention typically include a conductive constituent disposed upon the base constituent that includes at least one electrode for contacting an analyte or its byproduct (e.g. oxygen and/or hydrogen peroxide) to be assayed (see, e.g. element 104 in FIG. 2). The term "conductive constituent" is used herein according to art accepted terminology and refers to electrically conductive sensor elements such as a plurality of electrically conductive members disposed on the base layer in an array (e.g. so as to form a microarray electrode) and which are capable of measuring a detectable signal and conducting this to a detection apparatus. An illustrative example of this is a conductive constituent that forms a working electrode that can measure an increase or decrease in current in response to exposure to a stimuli such as the change in the concentration of an analyte or its byproduct as compared to a reference electrode that does not experience the change in the concentration of the analyte, a coreactant (e.g. oxygen) used when the analyte interacts with a composition (e.g. the enzyme glucose oxidase) present in analyte sensing constituent 110 or a reaction product of this interaction (e.g. hydrogen peroxide). Illustrative examples of such elements include electrodes which are capable of producing variable detectable signals in the presence of variable concentrations of molecules such as hydrogen peroxide or oxygen.

In addition to the working electrode, the analyte sensors of the invention typically include a reference electrode or a combined reference and counter electrode (also termed a quasi-reference electrode or a counter/reference electrode). If the sensor does not have a counter/reference electrode then it may include a separate counter electrode, which may be made from the same or different materials as the working electrode. Typical sensors of the present invention have one or more working electrodes and one or more counter, reference, and/or counter/reference electrodes. One embodiment of the sensor of the present invention has two, three or four or more working electrodes. These working electrodes in the sensor may be integrally connected or they may be kept separate. Optionally, the electrodes can be disposed on a single surface or side of the sensor structure. Alternatively, the electrodes can be disposed on a multiple surfaces or sides of the sensor structure (and can for example be connected by vias through the sensor material(s) to the surfaces on which the electrodes are disposed). In certain embodiments of the invention, the reactive surfaces of the electrodes are of different relative areas/sizes, for example a 1X reference electrode, a 2.6X working electrode and a 3.6X counter electrode.

Interference Rejection Constituent

The electrochemical sensors of the invention optionally include an interference rejection constituent disposed between the surface of the electrode and the environment to be assayed. In particular, certain sensor embodiments rely on the oxidation and/or reduction of hydrogen peroxide generated by enzymatic reactions on the surface of a working electrode at a constant potential applied. Because amperometric detection based on direct oxidation of hydrogen peroxide requires a relatively high oxidation potential, sensors employing this detection scheme may suffer interference from oxidizable species that are present in biological fluids such as ascorbic acid, uric acid and acetaminophen. In this context, the term "interference rejection constituent" is used herein according to art accepted terminology and refers to a coating or membrane in the sensor that functions to inhibit spurious signals generated by such oxidizable species which interfere with the detection of the signal generated by the analyte to be sensed. Certain interference rejection constituents function via size exclusion (e.g. by excluding interfering species of a specific size). Examples of interference rejection constituents include one or more layers or coatings of compounds such as hydrophilic polyurethanes, cellulose acetate (including cellulose acetate incorporating agents such as poly(ethylene glycol), polyethersulfones, polytetra-fluoroethylenes, the perfluoronated ionomer Nafion™, polyphenylenediamine, epoxy and the like.

Analyte Sensing Constituent

The electrochemical sensors of the invention include an analyte sensing constituent disposed on the electrodes of the sensor (see, e.g. element 110 in FIG. 2). The term "analyte sensing constituent" is used herein according to art accepted terminology and refers to a constituent comprising a material that is capable of recognizing or reacting with an analyte whose presence is to be detected by the analyte sensor apparatus. Typically this material in the analyte sensing constituent produces a detectable signal after interacting with the analyte to be sensed, typically via the electrodes of the conductive constituent. In this regard, the analyte sensing constituent and the electrodes of the conductive constituent work in combination to produce the electrical signal that is read by an apparatus associated with the analyte sensor. Typically, the analyte sensing constituent comprises an oxidoreductase enzyme capable of reacting with and/or producing a molecule whose change in concentration can be measured by measuring the change in the current at an electrode of the conductive constituent (e.g. oxygen and/or hydrogen peroxide), for example the enzyme glucose oxidase. An enzyme capable of producing a molecule such as hydrogen peroxide can be disposed on the electrodes according to a number of processes known in the art. The analyte sensing constituent can coat all or a portion of the various electrodes of the sensor. In this context, the analyte sensing constituent may coat the electrodes to an equivalent degree. Alternatively, the analyte sensing constituent may coat different electrodes to different degrees, with for example the coated surface of the working electrode being larger than the coated surface of the counter and/or reference electrode.

Typical sensor embodiments of this element of the invention utilize an enzyme (e.g. glucose oxidase) that has been combined with a second protein (e.g. albumin) in a fixed ratio (e.g. one that is typically optimized for glucose oxidase stabilizing properties) and then applied on the surface of an electrode to form a thin enzyme constituent. In a typical embodiment, the analyte sensing constituent comprises a GOx and HSA mixture. In a typical embodiment of an analyte sensing constituent having GOx, the GOx reacts with glucose present in the sensing environment (e.g. the body of a mammal) and generates hydrogen peroxide.

As noted above, the enzyme and the second protein (e.g. an albumin) are typically treated to form a crosslinked matrix (e.g. by adding a cross-linking agent to the protein mixture). As is known in the art, crosslinking conditions may be manipulated to modulate factors such as the retained biological activity of the enzyme, its mechanical and/or operational stability. Illustrative crosslinking procedures are described in U.S. patent application Ser. No. 10/335,506 and PCT publication WO 03/035891 which are incorporated herein by reference. For example, an amine cross-linking reagent, such as, but not limited to, glutaraldehyde, can be added to the protein mixture. The addition of a cross-linking reagent to the protein mixture creates a protein paste. The concentration of the cross-linking reagent to be added may vary according to the concentration of the protein mixture. While glutaraldehyde is an illustrative crosslinking reagent, other cross-linking reagents may also be used or may be used in place of glutaraldehyde. Other suitable cross-linkers also may be used, as will be evident to those skilled in the art.

As noted above, in some embodiments of the invention, the analyte sensing constituent includes an agent (e.g. glucose oxidase) capable of producing a signal (e.g. a change in oxygen and/or hydrogen peroxide concentrations) that can be sensed by the electrically conductive elements (e.g. electrodes which sense changes in oxygen and/or hydrogen peroxide concentrations). However, other useful analyte sensing constituents can be formed from any composition that is capable of producing a detectable signal that can be sensed by the electrically conductive elements after interacting with a target analyte whose presence is to be detected. In some embodiments, the composition comprises an enzyme that modulates hydrogen peroxide concentrations upon reaction with an analyte to be sensed. Alternatively, the composition comprises an enzyme that modulates oxygen concentrations upon reaction with an analyte to be sensed. In this context, a wide variety of enzymes that either use or produce hydrogen peroxide and/or oxygen in a reaction with a physiological analyte are known in the art and these enzymes can be readily incorporated into the analyte sensing constituent composition. A variety of other enzymes known in the art can produce and/or utilize compounds whose modulation can be detected by electrically conductive elements such as the electrodes that are incorporated into the sensor designs described herein. Such enzymes include for example, enzymes specifically described in Table 1, pages 15-29 and/or Table 18, pages 111-112 of Protein Immobilization: Fundamentals and Applications (Bioprocess Technology, Vol 14) by Richard F. Taylor (Editor) Publisher: Marcel Dekker; Jan. 7, 1991) the entire contents of which are incorporated herein by reference.

Protein Constituent

The electrochemical sensors of the invention optionally include a protein constituent disposed between the analyte sensing constituent and the analyte modulating constituent (see, e.g. element 116 in FIG. 2). The term "protein constituent" is used herein according to art accepted terminology and refers to constituent containing a carrier protein or the like that is selected for compatibility with the analyte sensing constituent and/or the analyte modulating constituent. In typical embodiments, the protein constituent comprises an albumin such as human serum albumin. The HSA concentration may vary between about 0.5%--30% (w/v). Typically the HSA concentration is about 1-10% w/v, and most typically is about 5% w/v. In alternative embodiments of the invention, collagen or BSA or other structural proteins used in these contexts can be used instead of or in addition to HSA. This constituent is typically crosslinked on the analyte sensing constituent according to art accepted protocols.

Adhesion Promoting Constituent

The electrochemical sensors of the invention can include one or more adhesion promoting (AP) constituents (see, e.g. element 114 in FIG. 2). The term "adhesion promoting constituent" is used herein according to art accepted terminology and refers to a constituent that includes materials selected for their ability to promote adhesion between adjoining constituents in the sensor. Typically, the adhesion promoting constituent is disposed between the analyte sensing constituent and the analyte modulating constituent. Typically, the adhesion promoting constituent is disposed between the optional protein constituent and the analyte modulating constituent. The adhesion promoter constituent can be made from any one of a wide variety of materials known in the art to facilitate the bonding between such constituents and can be applied by any one of a wide variety of methods known in the art. Typically, the adhesion promoter constituent comprises a silane compound such as γ-aminopropyltrimethoxysilane.

Analyte Modulating Constituent

The electrochemical sensors of the invention include an analyte modulating constituent disposed on the sensor (see, e.g. element 112 in FIG. 2). The term "analyte modulating constituent" is used herein according to art accepted terminology and refers to a constituent that typically forms a membrane on the sensor that operates to modulate the diffusion of one or more analytes, such as glucose, through the constituent. In certain embodiments of the invention, the analyte modulating constituent is an analyte-limiting membrane which operates to prevent or restrict the diffusion of one or more analytes, such as glucose, through the constituents. In other embodiments of the invention, the analyte-modulating constituent operates to facilitate the diffusion of one or more analytes, through the constituents. Optionally such analyte modulating constituents can be formed to prevent or restrict the diffusion of one type of molecule through the constituent (e.g. glucose), while at the same time allowing or even facilitating the diffusion of other types of molecules through the constituent (e.g. $O_2$).

With respect to glucose sensors, in known enzyme electrodes, glucose and oxygen from blood, as well as some interferants, such as ascorbic acid and uric acid, diffuse through a primary membrane of the sensor. As the glucose, oxygen and interferants reach the analyte sensing constituent, an enzyme, such as glucose oxidase, catalyzes the conversion of glucose to hydrogen peroxide and gluconolactone. The hydrogen peroxide may diffuse back through the analyte modulating constituent, or it may diffuse to an electrode where it can be reacted to form oxygen and a proton to produce a current that is proportional to the glucose concentration. The analyte modulating sensor membrane assembly serves several functions, including selectively allowing the passage of glucose therethrough (see, e.g. U.S. Patent Application No. 2011-0152654).

Cover Constituent

The electrochemical sensors of the invention include one or more cover constituents which are typically electrically insulating protective constituents (see, e.g. element 106 in FIG. 2). Typically, such cover constituents can be in the form of a coating, sheath or tube and are disposed on at least a portion of the analyte modulating constituent. Typically such features comprise a polymer comprising a surface having the constellation of features disclosed herein that function to modulate immune response. Acceptable polymer coatings for use as the insulating protective cover constituent can include, but are not limited to, non-toxic biocompatible polymers such as silicone compounds, polyimides, biocompatible solder masks, epoxy acrylate copolymers, or the like. Further, these coatings can be photo-imageable to facilitate photolithographic forming of apertures through to the conductive constituent. A typical cover constituent comprises spun on silicone. As is known in the art, this constituent can be a commercially available RTV (room temperature vulcanized) silicone composition. A typical chemistry in this context is polydimethyl siloxane (acetoxy based).

C. Typical Analyte Sensor System Embodiments of the Invention

Embodiments of the sensor elements and sensors can be operatively coupled to a variety of other system elements typically used with analyte sensors (e.g. structural elements such as piercing members, insertion sets and the like as well as electronic components such as processors, monitors, medication infusion pumps and the like), for example to adapt them for use in various contexts (e.g. implantation within a mammal). One embodiment of the invention includes a method of monitoring a physiological characteristic of a user using an embodiment of the invention that includes an input element capable of receiving a signal from a sensor that is based on a sensed physiological characteristic value of the user, and a processor for analyzing the received signal. In typical embodiments of the invention, the processor determines a dynamic behavior of the physiological characteristic value and provides an observable indicator based upon the dynamic behavior of the physiological characteristic value so determined. In some embodiments, the physiological characteristic value is a measure of the concentration of blood glucose in the user. In other embodiments, the process of analyzing the received signal and determining a dynamic behavior includes repeatedly measuring the physiological characteristic value to obtain a series of physiological characteristic values in order to, for example, incorporate comparative redundancies into a sensor apparatus in a manner designed to provide confirmatory information on sensor function, analyte concentration measurements, the presence of interferences and the like.

FIG. 11 in U.S. Patent Publication 2014/0163346 shows a schematic of a potentiostat that may be used to measure current in embodiments of the present invention. As shown in FIG. 11 in U.S. Patent Publication 2014/0163346, a potentiostat 300 may include an op amp 310 that is connected in an electrical circuit so as to have two inputs: Vset and Vmeasured. As shown, Vmeasured is the measured value of the voltage between a reference electrode and a working electrode. Vset, on the other hand, is the optimally desired voltage across the working and reference electrodes. The current between the counter and reference electrode is measured, creating a current measurement (isig) that is output from the potentiostat.

Embodiments of the invention include devices which process display data from measurements of a sensed physiological characteristic (e.g. blood glucose concentrations) in a manner and format tailored to allow a user of the device to easily monitor and, if necessary, modulate the physiological status of that characteristic (e.g. modulation of blood glucose concentrations via insulin administration). An illustrative embodiment of the invention is a device comprising a sensor input capable of receiving a signal from a sensor, the signal being based on a sensed physiological characteristic value of a user; a memory for storing a plurality of measurements of the sensed physiological characteristic value of the user from the received signal from the sensor; and a display for presenting a text and/or graphical representation of the plurality of measurements of the sensed physiological characteristic value (e.g. text, a line graph or the like, a bar graph or the like, a grid pattern or the like or a combination thereof). Typically, the graphical representation displays real time measurements of the sensed physiological characteristic value. Such devices can be used in a variety of contexts, for example in combination with other medical apparatuses. In some embodiments of the invention, the device is used in combination with at least one other medical device (e.g. a glucose sensor).

An illustrative system embodiment consists of a glucose sensor, a transmitter and pump receiver and a glucose meter. In this system, radio signals from the transmitter can be sent to the pump receiver every 5 minutes to provide providing real-time sensor glucose (SG) values. Values/graphs are displayed on a monitor of the pump receiver so that a user can self monitor blood glucose and deliver insulin using their own insulin pump. Typically, an embodiment of device disclosed herein communicates with a second medical device via a wired or wireless connection. Wireless communication can include for example the reception of emitted radiation signals as occurs with the transmission of signals via RF telemetry, infrared transmissions, optical transmission, sonic and ultrasonic transmissions and the like. Optionally, the device is an integral part of a medication infusion pump (e.g. an insulin pump). Typically, in such devices, the physiological characteristic values include a plurality of measurements of blood glucose.

FIG. 3 provides a perspective view of one generalized embodiment of subcutaneous sensor insertion system and a block diagram of a sensor electronics device according to one illustrative embodiment of the invention. Additional elements typically used with such sensor system embodiments are disclosed for example in U.S. Patent Application No. 20070163894, the contents of which are incorporated by reference. FIG. 3 provides a perspective view of a telemetered characteristic monitor system 1, including a subcutaneous sensor set 10 provided for subcutaneous placement of an active portion of a flexible sensor 12, or the like, at a selected site in the body of a user. The subcutaneous or percutaneous portion of the sensor set 10 includes a hollow, slotted insertion needle 14 having a sharpened tip 44, and a cannula 16. Inside the cannula 16 is a sensing portion 18 of the sensor 12 to expose one or more sensor electrodes 20 to the user's bodily fluids through a window 22 formed in the cannula 16. The sensing portion 18 is joined to a connection portion 24 that terminates in conductive contact pads, or the like, which are also exposed through one of the insulative layers. The connection portion 24 and the contact pads are generally adapted for a direct wired electrical connection to a suitable monitor 200 coupled to a display 214 for monitoring a user's condition in response to signals derived from the sensor electrodes 20. The connection portion 24 may be conveniently connected electrically to the monitor 200 or a characteristic monitor transmitter 100 by a connector block 28 (or the like).

As shown in FIG. 3, in accordance with embodiments of the present invention, subcutaneous sensor set 10 may be configured or formed to work with either a wired or a wireless characteristic monitor system. The proximal part of the sensor 12 is mounted in a mounting base 30 adapted for placement onto the skin of a user. The mounting base 30 can be a pad having an underside surface coated with a suitable pressure sensitive adhesive layer 32, with a peel-off paper strip 34 normally provided to cover and protect the adhesive layer 32, until the sensor set 10 is ready for use. The mounting base 30 includes upper and lower layers 36 and 38, with the connection portion 24 of the flexible sensor 12 being sandwiched between the layers 36 and 38. The connection portion 24 has a forward section joined to the active sensing portion 18 of the sensor 12, which is folded angularly to extend downwardly through a bore 40 formed in the lower base layer 38. Optionally, the adhesive layer 32 (or another portion of the apparatus in contact with in vivo tissue) includes an anti-inflammatory agent to reduce an inflammatory response and/or anti-bacterial agent to reduce the chance of infection. The insertion needle 14 is adapted for slide-fit reception through a needle port 42 formed in the upper base layer 36 and through the lower bore 40 in the lower base layer 38. After insertion, the insertion needle 14 is withdrawn to leave the cannula 16 with the sensing portion 18 and the sensor electrodes 20 in place at the selected insertion site. In this embodiment, the telemetered characteristic monitor transmitter 100 is coupled to a sensor set 10 by a cable 102 through a connector 104 that is electrically coupled to the connector block 28 of the connector portion 24 of the sensor set 10.

In the embodiment shown in FIG. 3, the telemetered characteristic monitor 100 includes a housing 106 that supports a printed circuit board 108, batteries 110, antenna 112, and the cable 102 with the connector 104. In some embodiments, the housing 106 is formed from an upper case 114 and a lower case 116 that are sealed with an ultrasonic weld to form a waterproof (or resistant) seal to permit cleaning by immersion (or swabbing) with water, cleaners, alcohol or the like. In some embodiments, the upper and lower case 114 and 116 are formed from a medical grade plastic. However, in alternative embodiments, the upper case 114 and lower case 116 may be connected together by other methods, such as snap fits, sealing rings, RTV (silicone sealant) and bonded together, or the like, or formed from other materials, such as metal, composites, ceramics, or the like. In other embodiments, the separate case can be eliminated and the assembly is simply potted in epoxy or other moldable materials that is compatible with the electronics and reasonably moisture resistant. As shown, the lower case 116 may have an underside surface coated with a suitable pressure sensitive adhesive layer 118, with a peel-off paper strip 120 normally provided to cover and protect the adhesive layer 118, until the sensor set telemetered characteristic monitor transmitter 100 is ready for use.

In the illustrative embodiment shown in FIG. 3, the subcutaneous sensor set 10 facilitates accurate placement of a flexible thin film electrochemical sensor 12 of the type used for monitoring specific blood parameters representative of a user's condition. The sensor 12 monitors glucose levels in the body, and may be used in conjunction with automated or semi-automated medication infusion pumps of the external or implantable type as described in U.S. Pat. No. 4,562,751; 4,678,408; 4,685,903 or 4,573,994, to control delivery of insulin to a diabetic patient.

In the illustrative embodiment shown in FIG. 3, the sensor electrodes 10 may be used in a variety of sensing applications and may be configured in a variety of ways. For example, the sensor electrodes 10 may be used in physiological parameter sensing applications in which some type of biomolecule is used as a catalytic agent. For example, the sensor electrodes 10 may be used in a glucose and oxygen sensor having a glucose oxidase enzyme catalyzing a reaction with the sensor electrodes 20. The sensor electrodes 10, along with a biomolecule or some other catalytic agent, may be placed in a human body in a vascular or non-vascular environment. For example, the sensor electrodes 20 and biomolecule may be placed in a vein and be subjected to a blood stream, or may be placed in a subcutaneous or peritoneal region of the human body.

In the embodiment of the invention shown in FIG. 3, the monitor of sensor signals 200 may also be referred to as a sensor electronics device 200. The monitor 200 may include a power source, a sensor interface, processing electronics (i.e. a processor), and data formatting electronics. The monitor 200 may be coupled to the sensor set 10 by a cable 102 through a connector that is electrically coupled to the connector block 28 of the connection portion 24. In an alternative embodiment, the cable may be omitted. In this embodiment of the invention, the monitor 200 may include an appropriate connector for direct connection to the connection portion 104 of the sensor set 10. The sensor set 10 may be modified to have the connector portion 104 positioned at a different location, e.g., on top of the sensor set to facilitate placement of the monitor 200 over the sensor set.

While the analyte sensor and sensor systems disclosed herein are typically designed to be implantable within the body of a mammal, the inventions disclosed herein are not limited to any particular environment and can instead be used in a wide variety of contexts, for example for the analysis of most in vivo and in vitro liquid samples including biological fluids such as interstitial fluids, whole-blood, lymph, plasma, serum, saliva, urine, stool, perspiration, mucus, tears, cerebrospinal fluid, nasal secretion, cervical or vaginal secretion, semen, pleural fluid, amniotic fluid, peritoneal fluid, middle ear fluid, joint fluid, gastric aspirate or the like. In addition, solid or desiccated samples may be dissolved in an appropriate solvent to provide a liquid mixture suitable for analysis.

It is to be understood that this invention is not limited to the particular embodiments described, as such may, of course, vary. It is also to be understood that the terminology used herein is for the purpose of describing particular embodiments only, and is not intended to be limiting, since the scope of the present invention will be limited only by the appended claims. In the description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

The invention claimed is:

1. A method of avoiding an inflammatory response to an implanted medical device comprising implanting the implantable medical device having a surface adapted to contact an in vivo environment, the surface comprising a polyimide composition having the following characteristics:
   a carbon-to-oxygen ratio greater than 5 to 1;
   a surface hydrophobicity of between 75° and 90°;
   a surface topography characterized by at least one of (a)-(c):
   (a) grooves having an average peak-to-valley height of between 0.3 μm and 5 μm;
   (b) wells having an average peak-to-valley height of between 1 μm and 2 μm; and
   (c) grids having an average peak-to-valley height of between 2 μm and 4 μm;
   wherein:
   the surface avoids the inflammatory response by having surface characteristics such that when exposed to the surface comprising the polymer composition, RAW264.7 macrophages are influenced to differentiate into an anti-inflammatory (M2) phenotype.

2. The method of claim 1, wherein the implantable medical device is implanted in an interstitial space.

3. The method of claim 1, wherein the implantable medical device is a glucose sensor.

4. A polymer composition that forms a surface comprising:
   a carbon-to-oxygen ratio greater than 5 to 1;
   a surface hydrophobicity of between 75° and 90°;
   a surface topography characterized by at least one of (a)-(c):
   (a) grooves having an average peak-to-valley height of between 0.3 μm and 5 μm;
   (b) wells having an average peak-to-valley height of between 1 μm and 2 μm; and
   (c) grids having an average peak-to-valley height of between 2 μm and 4 μm;

wherein:

when exposed to the surface, RAW264.7 macrophages are influenced to differentiate into an anti-inflammatory (M2) phenotype.

* * * * *